United States Patent
Chu

(10) Patent No.: US 7,825,346 B2
(45) Date of Patent: Nov. 2, 2010

(54) LOW POWERED ACTIVATION ELECTRONIC DEVICE

(76) Inventor: Jack Chu, 1508-1510, 15/F, Tower II, Silvercord, 30 Canton Rd., Tsim Sha Tsui, Kowloon (HK)

( * ) Notice: Subject to any disclaimer, the term of this patent is extended or adjusted under 35 U.S.C. 154(b) by 704 days.

(21) Appl. No.: 11/724,960

(22) Filed: Mar. 16, 2007

(65) Prior Publication Data

US 2007/0162156 A1   Jul. 12, 2007

Related U.S. Application Data

(63) Continuation-in-part of application No. 11/212,990, filed on Aug. 26, 2005, now Pat. No. 7,405,372.

(51) Int. Cl.
*H01H 9/00* (2006.01)
(52) U.S. Cl. .............. 200/511; 200/52 R; 446/175
(58) Field of Classification Search ........... 200/5 R, 200/600, 511, 512; 446/297, 175, 369, 485, 446/397; 341/20, 22, 33, 34; 345/156, 168, 345/173, 174
See application file for complete search history.

(56) References Cited

U.S. PATENT DOCUMENTS

| | | | | |
|---|---|---|---|---|
| 5,906,004 | A | * | 5/1999 | Lebby et al. ............... 2/1 |
| 6,210,771 | B1 | * | 4/2001 | Post et al. .............. 428/100 |
| 2005/0069695 | A1 | * | 3/2005 | Jung et al. ............. 428/328 |
| 2006/0035554 | A1 | * | 2/2006 | Glaser et al. ........... 442/301 |
| 2007/0089800 | A1 | * | 4/2007 | Sharma ................ 139/388 |
| 2008/0091097 | A1 | * | 4/2008 | Linti et al. ............. 600/389 |
| 2009/0088652 | A1 | * | 4/2009 | Tremblay .............. 600/509 |

* cited by examiner

*Primary Examiner*—Michael A Friedhofer
(74) *Attorney, Agent, or Firm*—Raymond Y. Chan; David and Raymond Patent Firm

(57) ABSTRACT

A low powered activation electronic device includes a power source, an electronic circuit, having two spaced apart electrodes, electrically connected to the power source to form an opened circuit, and two fabric contacts made of textile material provided at the two electrodes of the electronic circuit, wherein the electronic circuit is formed a closed circuit to activate the electronic device in responsive to a physical touch by a human operator at the two fabric contacts.

20 Claims, 12 Drawing Sheets

LOW POWERED ACTIVATION ELECTRONIC DEVICE

CROSS-REFERENCE OF RELATED APPLICATION

This is a continuation-in-part application of a non-provisional application having an application Ser. No. 11/212,990 and a filing date of Aug. 26, 2005 now U.S. Pat. No. 7,405,372.

BACKGROUND OF THE PRESENT INVENTION

1. Field of Invention

The present invention relates to an electronic apparatus, and more particularly to a low powered activation electric device which requires relatively low amperage for activation so as to allow human as a human conductor contacting with two conductive electrodes of an opened electronic circuit to form a closed electronic circuit in a human harmless manner.

2. Description of Related Arts

A conventional switch comprises a lever arranged to operate an electrical device between an "on" position and an "off" position by flicking the lever. An improved switch, which does not require any flicking movement of the lever, is a touch switch. Accordingly, the touch switch is a switch that is turned on and off by touching a wire contact. In comparison with the conventional switch, the touch switch require less mechanical part since the user is able to simply touch a conductor panel of the touch switch for activate the electrical device. However, such touch switch has several drawbacks.

Accordingly, since the touch switch requires the conductor panel contacting with a terminal of the opened circuit to form a closed circuit of the electrical device, an insulating film must be provided between the conductor panel and the terminal to prevent any mis-contact therebetween. Therefore, once the insulating film is worn off after a period of continuous use, the activation operation of the electrical device will be malfunctioned.

In addition, even though the touch switch does not require any flicking movement of the lever, the touch switch requires a slight displacement of the conductor panel to contact with the terminal of the circuit. However, the conductor panel will be eventually mis-aligned with the terminal of the circuit after a period of continuous use. In other words, the reliability of the touch switch will be gradually reduced.

Furthermore, the feeling of touching the conductor panel merely feels as touching a metal plate. Since the conductor panel is made of metal, the conductor panel losses its flexibility and textile feeling. In other words, the inherent feature of the metal plate limits the usage of the conductor panel. Thus, static always occurs at the conductor panel when the conductor is touched by human.

SUMMARY OF THE PRESENT INVENTION

A main object of the present invention is to provide a low powered activation electronic device which requires relatively low amperage for activation so as to allow human as a human conductor contacting with two conductive electrodes of an opened electronic circuit to form a closed electronic circuit in a human harmless manner.

Another object of the present invention is to provide a low powered activation electronic device, wherein the conductive electrodes are made of textile material so as to provide a textile feeling when touching the conductive electrodes to form a closed electronic circuit.

Another object of the present invention is to provide a low powered activation electronic device, wherein the conductive electrodes are made of stainless steel fiber (SSF) fabrics or other electro-conductive textile material, so as to provide versatility, flexibility, durability, softness, and unique feeling for touching. Therefore, the conductive electrodes are excellently used in toys and other related children's products.

Another object of the present invention is to provide a low powered activation electronic device, wherein no displacement of the conductive electrode is required to activate the electronic device so as to enhance the reliability of the conductive electrode for activation.

Another object of the present invention is to provide a low powered activation electronic device, wherein the activation of the electronic device is easy and simply by touching the two conductive electrodes such that a child is able to activate the electronic device by two hands.

Another object of the present invention is to provide a low powered activation electronic device, wherein no expensive or complicated structure is required to employ in the present invention in order to achieve the above mentioned objects. Therefore, the present invention successfully provides an economic and efficient solution not only for providing a circuit configuration for the electronic device but also for broadening the application of the conductive electrode.

Accordingly, in order to accomplish the above objects, the present invention provides a low powered activation electronic device, comprising:

a power source;

an electronic circuit, having two spaced apart electrodes, electrically connected to the power source to form an opened circuit; and two fabric contacts made of textile material provided at the two electrodes of the electronic circuit, wherein the electronic circuit is formed a closed circuit to activate the electronic device in responsive to a physical touch by a human operator at the two fabric contacts.

These and other objectives, features, and advantages of the present invention will become apparent from the following detailed description, the accompanying drawings, and the appended claims.

DETAILED DESCRIPTION OF THE PREFERRED EMBODIMENT

Figure 1:
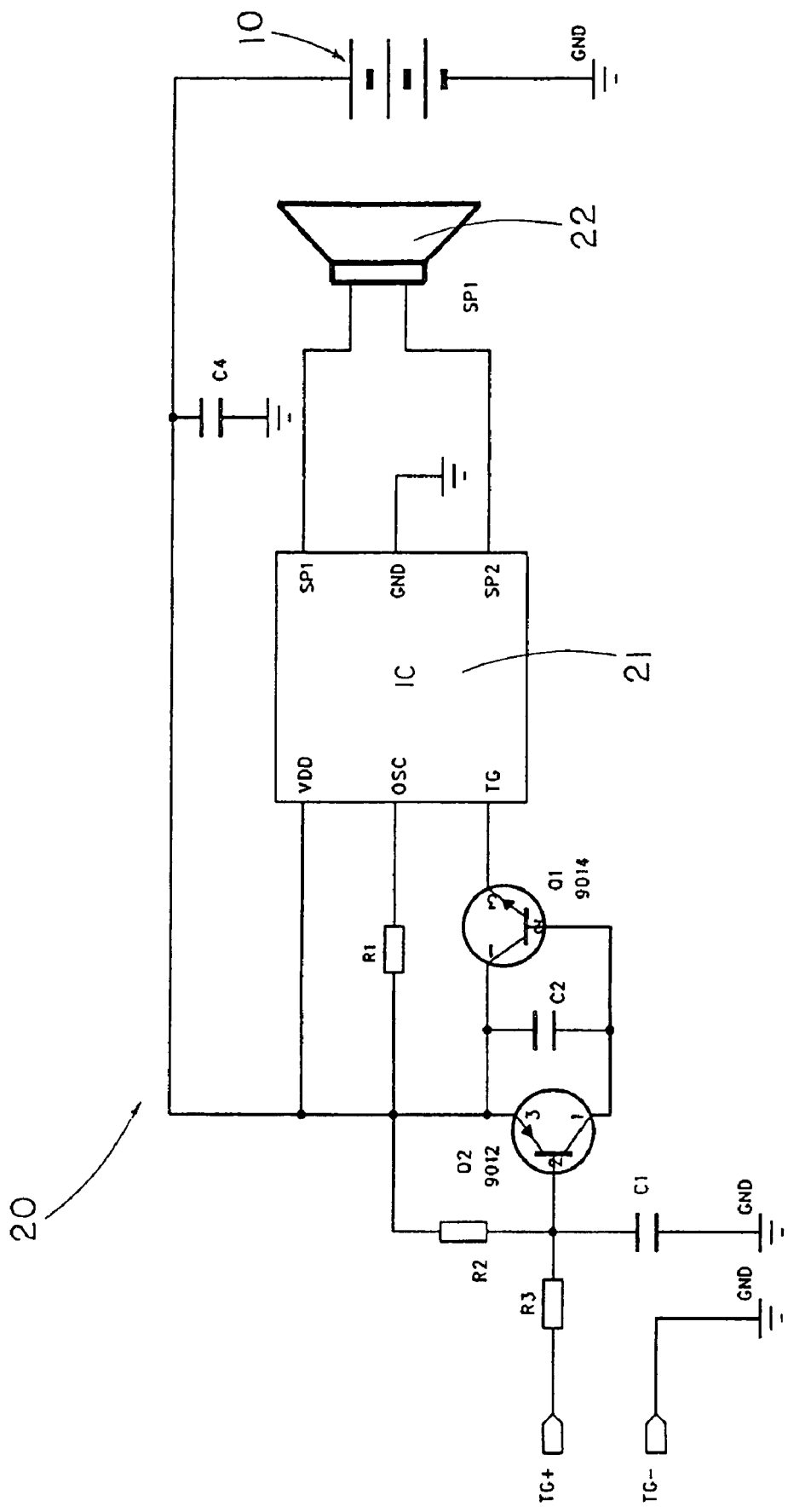
FIG. 1 is a circuit diagram of electronic circuit of a low powered activation electronic device according to a preferred embodiment of the present invention, illustrating the two fabric contacts.
Figure 2:
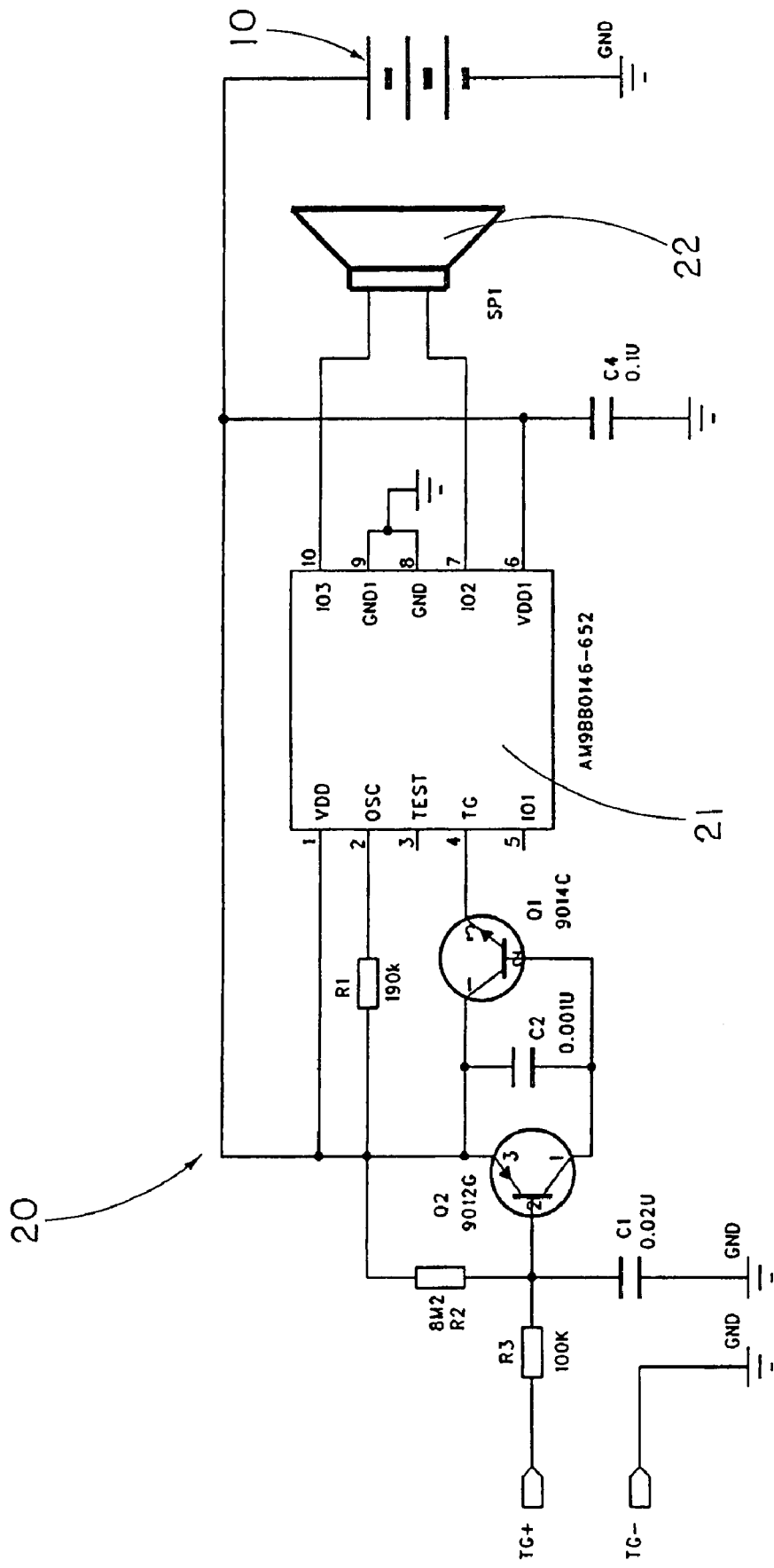
FIG. 2 illustrates a first alternative mode of the electronic circuit according to the above preferred embodiment of the present invention.
Figure 3:
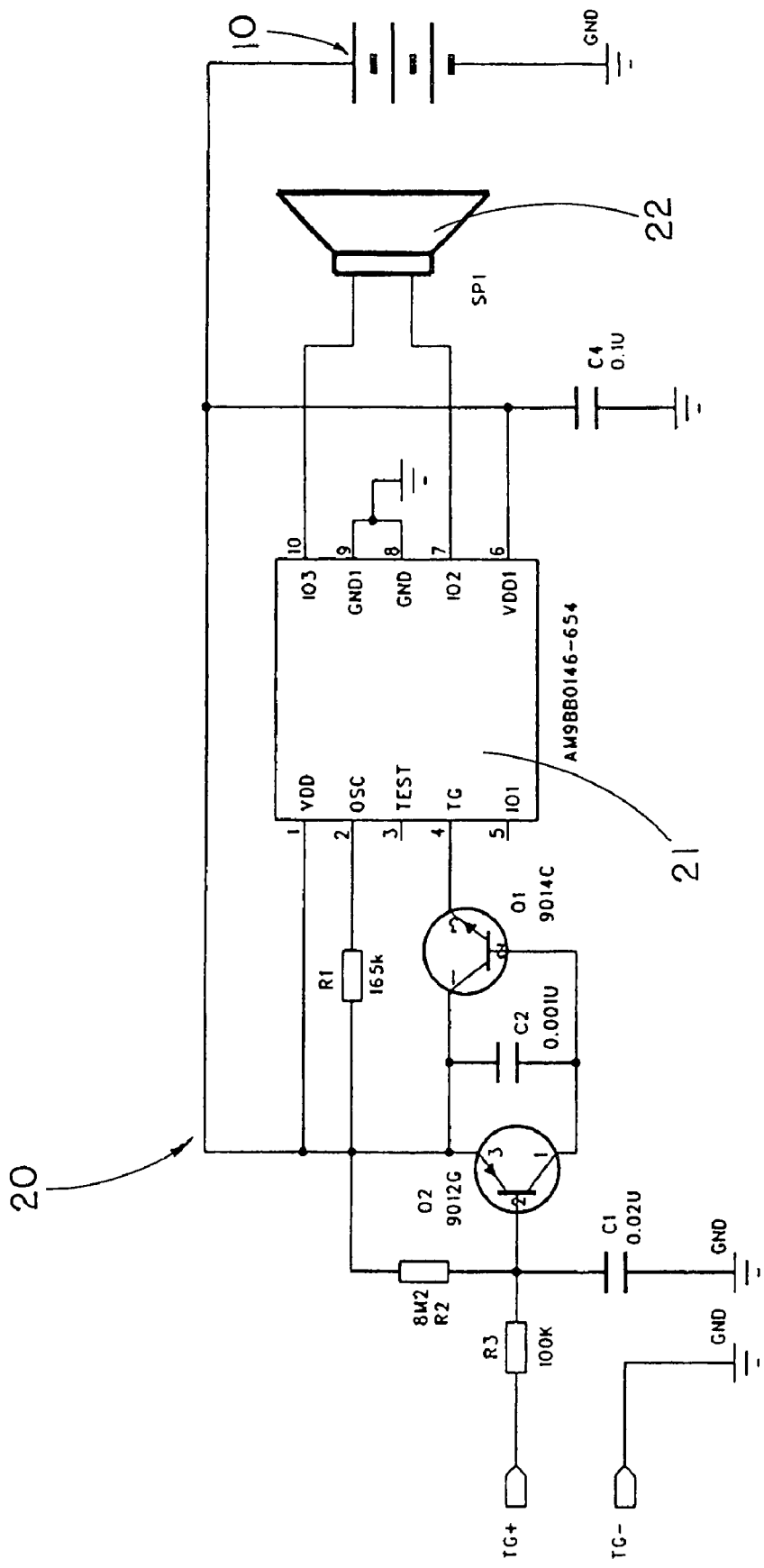
FIG. 3 illustrates a second alternative mode of the electronic circuit according to the above preferred embodiment of the present invention.
Figure 4:
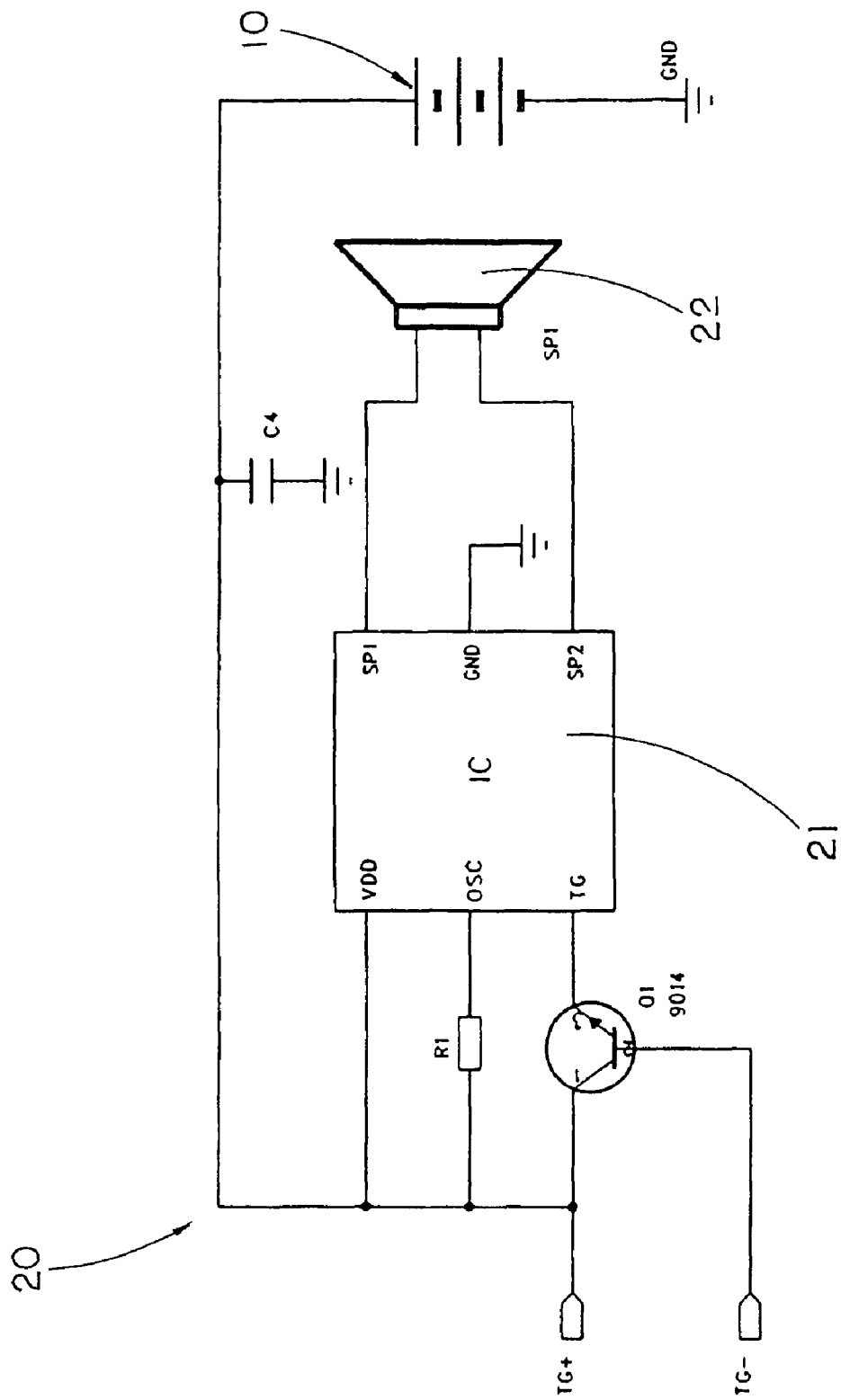
FIG. 4 illustrates a third alternative mode of the electronic circuit according to the above preferred embodiment of the present invention.
Figure 5:
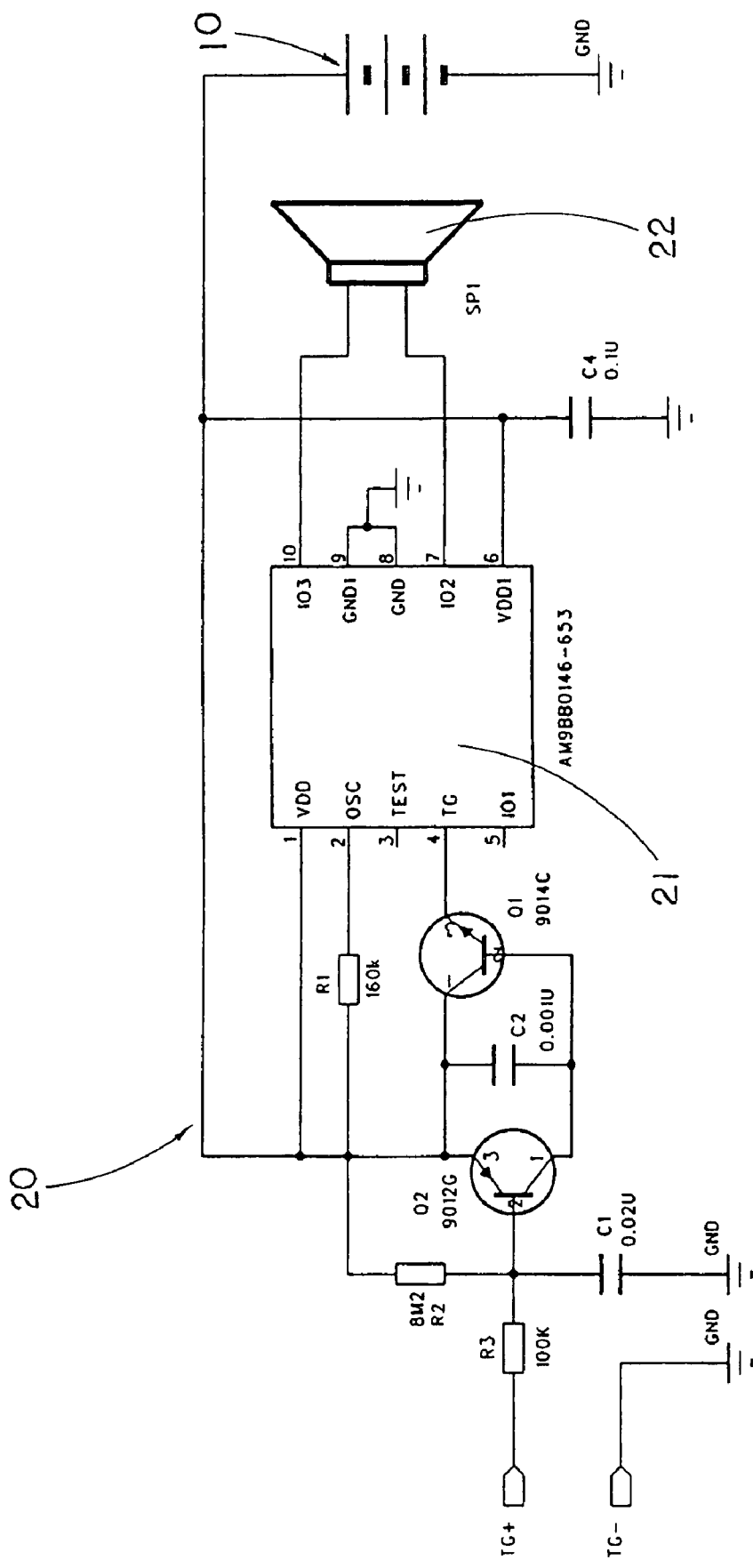
FIG. 5 illustrates a fourth alternative mode of the electronic circuit according to the above preferred embodiment of the present invention.
Figure 6:
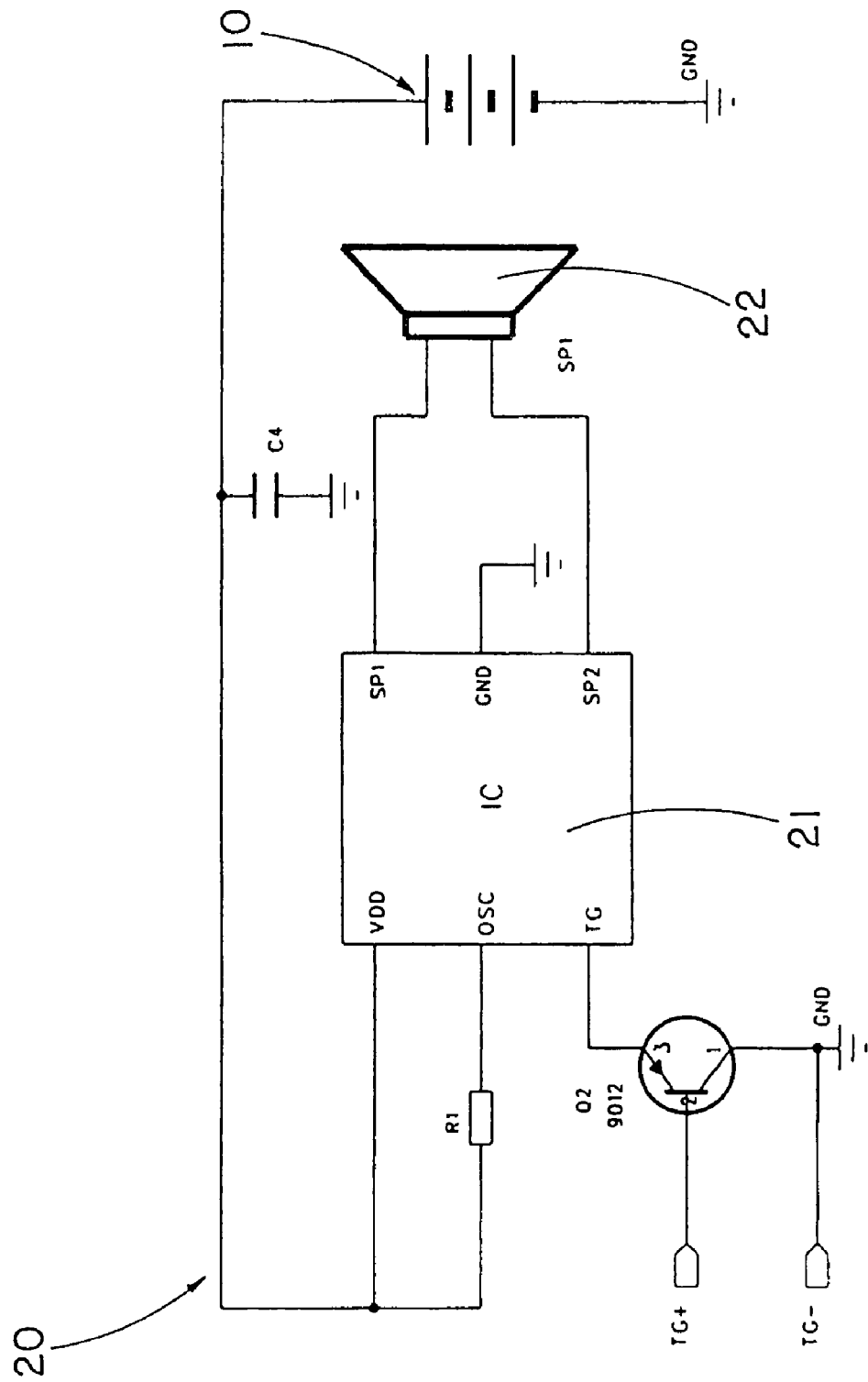
FIG. 6 illustrates a fifth alternative mode of the electronic circuit according to the above preferred embodiment of the present invention.
Figure 7:
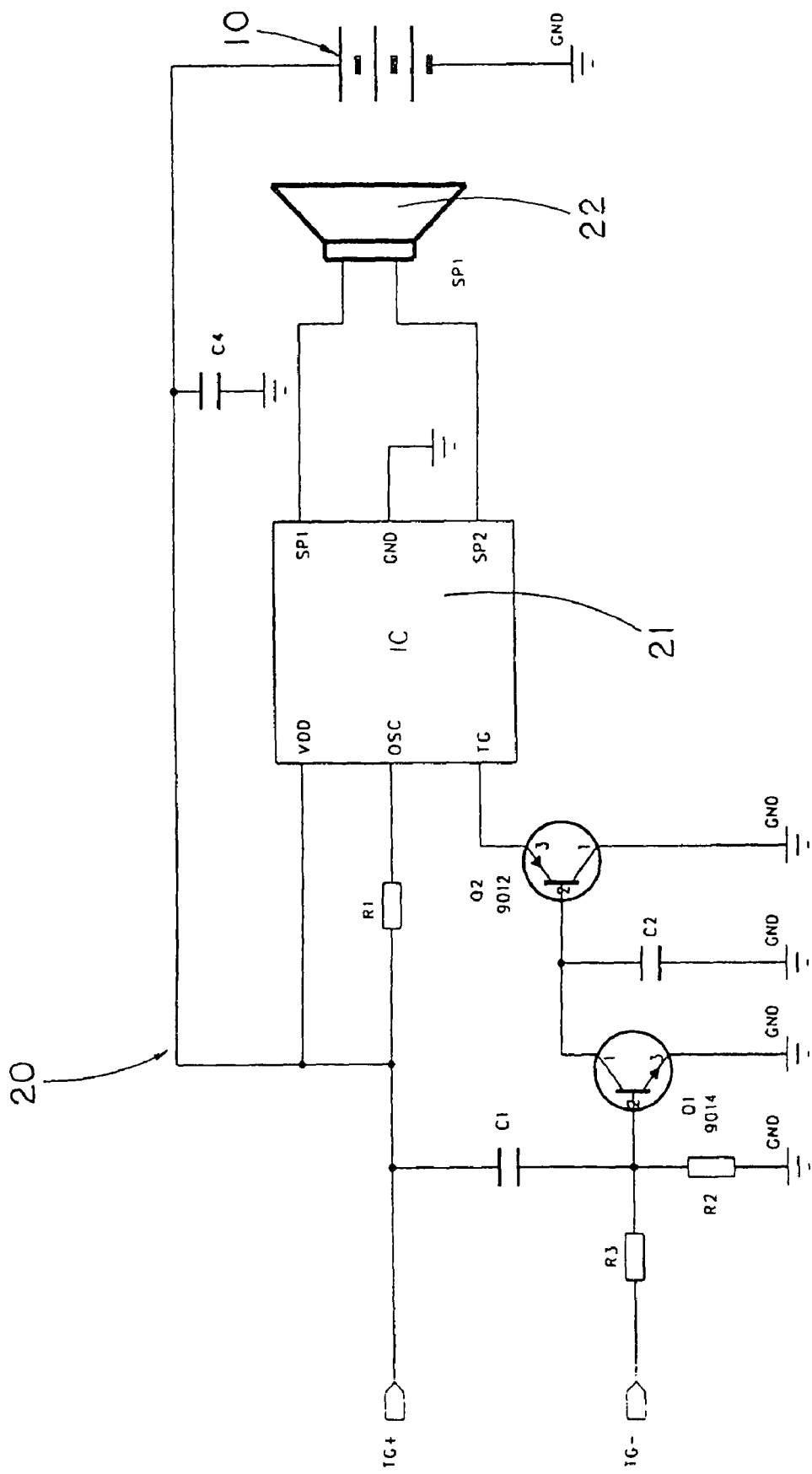
FIG. 7 illustrates a sixth alternative mode of the electronic circuit according to the above preferred embodiment of the present invention.

Referring to FIG. 1 of the drawings, a low powered activation electronic device according to a preferred embodiment of the present invention is illustrated, wherein the low powered activation electronic device comprises a power source 10, and an electronic circuit 20, having two spaced apart electrodes TC+, TC−, electrically connected to the power source 10 to form an opened circuit.

The low powered activation electronic device further comprises two fabric contacts 30 made of textile material provided at the two electrodes TC+, TC− of the electronic circuit 20, wherein the electronic circuit 20 is formed a closed circuit to activate the electronic device in responsive to a physical touch by a human operator at the two fabric contacts 30.

According to a preferred embodiment, the low powered activation electronic device of the present invention is especially designed for children's toy and other related electronic products. Since it requires a relatively low power to activate the electronic circuit 20, even a child is able to operate the electronic device without harming the child when the child touches the fabric contacts 30.

Figure 10:
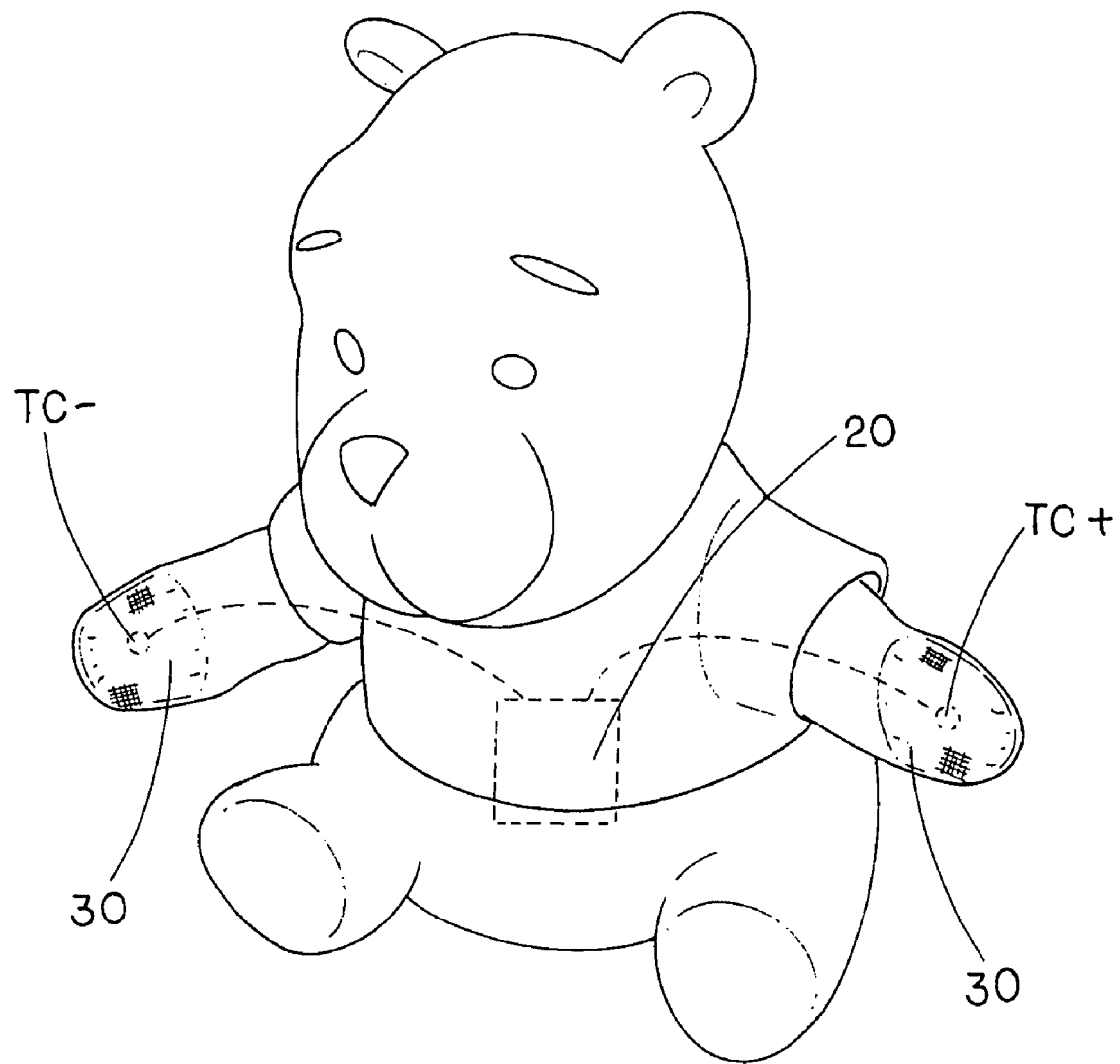
FIG. 10 illustrates an application of the low powered activation electronic device for a children's toy according to a preferred embodiment of the present invention.

As shown in FIG. 10, the low powered activation electronic device of the present invention is used in the children's toy, such as a doll, having an interior cavity. The power source 10 and the electronic circuit 20 are adapted for being disposed in the interior cavity of the children's toy, wherein the two electrodes TC+, TC− are extended from the electronic circuit 20 within the interior cavity of the children's toy. The two fabric contacts 30 are electrically coupled at the two electrodes TC+, TC− respectively at an outer surface of the children's toy.

For example, the two electrodes TC+, TC− are extended from the electronic circuit 20 and spacedly extended within the doll at two hands thereof while the fabric contacts 30 are integrally provided on the outer surface of the doll at two hand surfaces of the doll to contact with the electrodes TC+, TC− such that when the child touches the fabric contacts 30 of the doll, the electrodes TC+, TC− are electrically connected through the child to form a closed circuit of the electronic circuit 20 so as to activate the electronic device. It is worth to mention that the fabric contacts 30 can be positioned at two feet surfaces of the doll to contact with the electrodes TC+, TC− at two feet of the doll. Likewise, the fabric contacts 30 can be positioned at two ear surfaces of the doll to contact with the electrodes TC+, TC− at two ears of the doll to activate the electronic device when the child touches the ears of the doll. It is worth to mention that when the hands of the child touch the fabric contacts 30, the electrodes TC+, TC− are electrically connected through the child to form a closed circuit of the electronic circuit 20 so as to activate the electronic device. Thus, two or more children, holding their hands with each other, can form a human conductor to form the closed circuit of the electronic circuit 20 when the fabric contacts 30 are touched by the children.

Accordingly, the power source 10 comprises a replaceable battery electrically connected to the electronic circuit 20, wherein the power source 10 is replaceably disposed in the doll such that the power source 10 can be replaced when there is out of battery.

Each of the fabric contacts 30 is made of electro-conductive textile material such as stainless steel fiber (SSF) fabrics which provides versatility, flexibility, durability, softness, and unique feeling for touching.

Accordingly, SSF fabrics and other electro-conductive textile materials can be used as primary conduits to complete the opened circuit. But in this case, they are being used as intermediate or secondary electricity conductors. The human operator(s), such as the child, connects the opposite ends of electro-polarities by touching both conductive electrodes covered by SSF fabrics and other electro-conductive textile materials, which serve as the primary conductor to close the opened circuit, thereby activating the electronic device.

Figure 8:
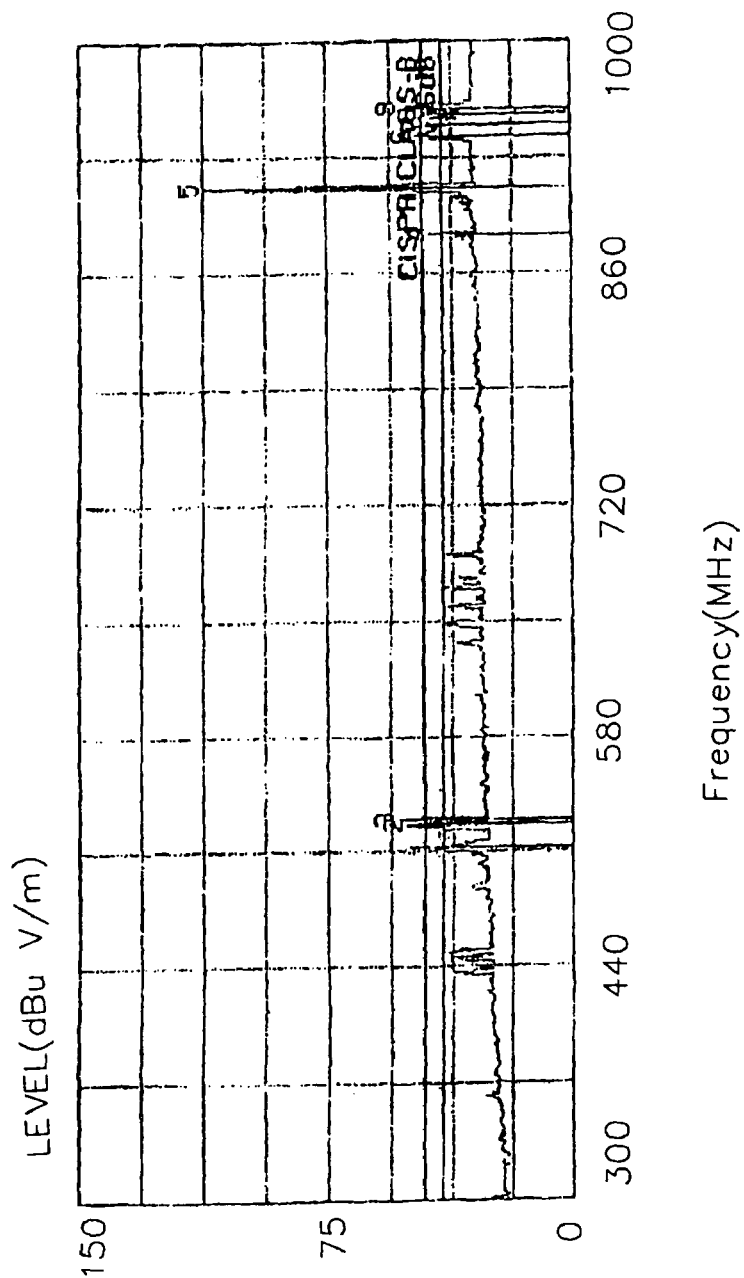
FIG. 8 illustrates the electro-conductive properties of the electronic circuit with the stainless steel fiber (SSF) fabrics according to the above preferred embodiment of the present invention.
Figure 9:
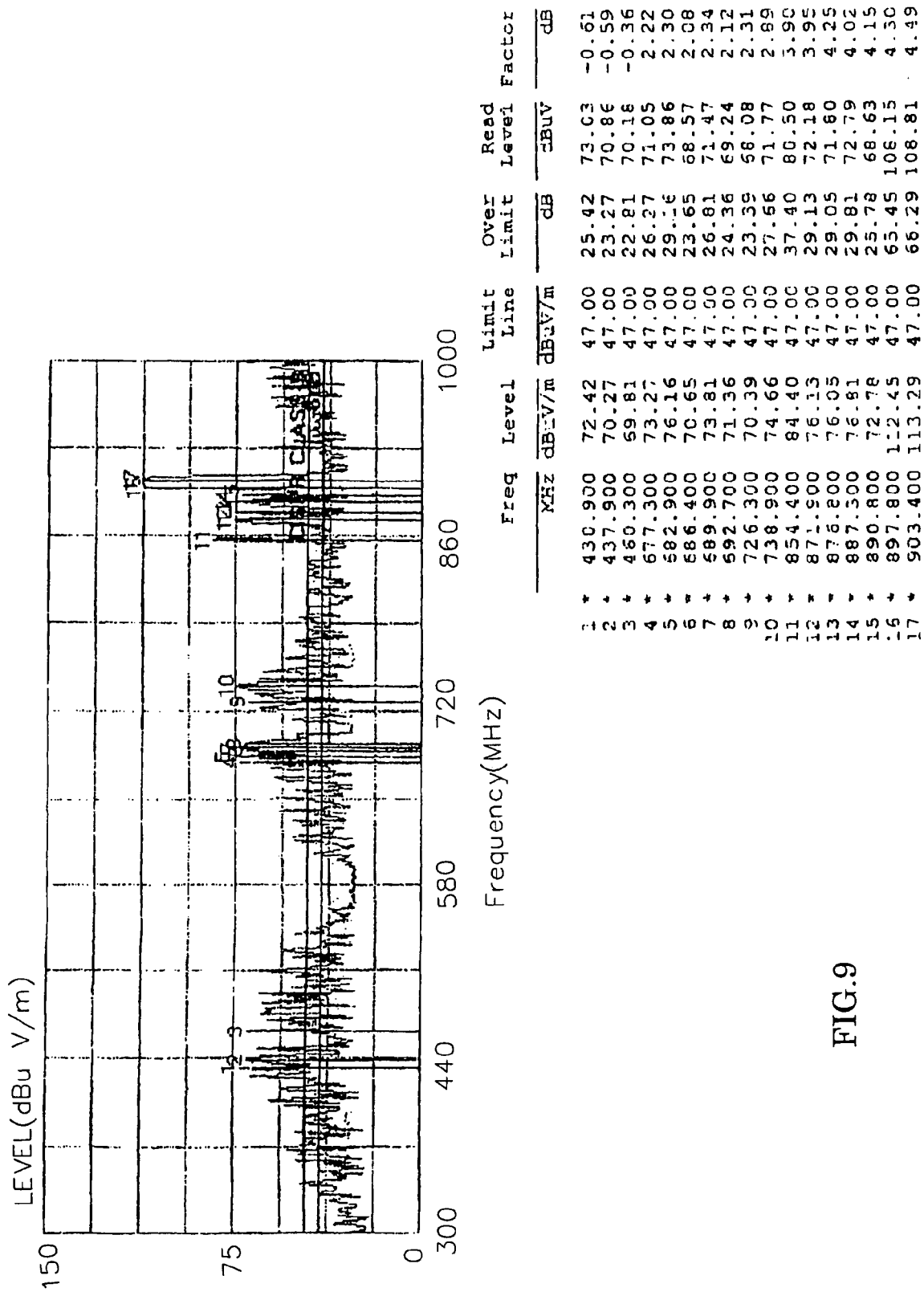
FIG. 9 illustrates the electro-conductive properties of the electronic circuit without the stainless steel fiber (SSF) fabrics according to the above preferred embodiment of the present invention.

The concept of the "human conductor" is not new, Humans are widely capably of being conductors of electric energy. At very low power levels (characterize by low amperage), little or no physical effect will be felt by the human operator as electric energy passes through the human body. However, the combination of 1) Human conductivity, and 2) The utilization of SSF fabrics or other electro-conductive textile materials, 3) The activation, operation, and/or termination of electronic devices, especially in children's toys and other related electronic products. Accordingly, FIGS. 8 and 9 are diagrams elaborating the application of the conductive fabric actually help out shielding off some electro-magnetic-inductance.

In other words, the activation of low powered battery operated electronic device is operated by the human operator(s) touching on both opposite ends of the electrodes covered by the fabric contacts 30 or other electro-conductive textile materials, thereby closing the opened electronic circuit.

The circuit diagrams of the low powered activation electronic device includes, but not limited to, FIG. 1, FIG. 2, FIG. 3, FIG. 4, FIG. 5, FIG. 6 and FIG. 7.

The electronic circuit 20 in FIG. 1, FIG. 2, FIG. 3, FIG. 4, FIG. 5, FIG. 6 and FIG. 7 are opened between points TG+ and TG−.

Once the opened circuits in TG+ and TG− are closed in FIG. 1, FIG. 2, FIG. 3, FIG. 4, FIG. 5, FIG. 6 and FIG. 7, the low powered activation electronic device will be activated.

The electrode in TG+ is covered by stainless steel fiber (SSF) fabrics or electro-conductive textile materials.

The electrode in TG− is covered by stainless steel fiber (SSF) fabrics or electro-conductive textile materials.

Electrodes in TG+ covered by stainless steel fiber (SSF) fabrics or electro-conductive textile materials are separated by non-conductive materials from the electrodes in TG− covered by stainless steel fiber (SSF) fabrics or electro-conductive textile materials.

The stainless steel fiber (SSF) fabrics or electro-conductive textile materials covering TG+ or TG− serve as intermediate or secondary conductors between the electrodes and the human operator.

The physical touch by human operator(s) connecting the opposite ends of the electrodes (TG+ and TG−) close the opened circuit in FIG. 1, FIG. 2, FIG. 3, FIG. 4, FIG. 5, FIG. 6 and FIG. 7, and thereby activates the low powered activation electronic device.

According to the preferred embodiment, the electronic circuit 20 can be configured as shown in FIGS. 1 to 7, wherein the electronic circuit 20 is configured by at least a triode, resistance, and capacitor. The electronic circuit 20 further comprises a memory module 21, i.e. the IC, having a pre-stored program therein and a circuit output 22 which is linked with the memory module 21 and is arranged when the electronic circuit 20 is activated, i.e. closing the opened circuit by touching the two electrodes TC+, TC−, the memory module 21 outputs an output signal to the circuit output 22.

As above mentioned example, the circuit output 22 comprises a speaker disposed in the doll, wherein the memory module 21 contains a musical program such that when the child touches the fabric contacts 30 to activate the electronic circuit 20, the memory module 21 output the musical signal as the output signal to the speaker of the circuit output 22 for broadcasting the music. Alternatively, the circuit output 22 can be a micro motor at the head of the doll such that when the electronic circuit 20 is activated, the micro motor is actuated to shake the head of the doll.

Alternatively, the low powered activation electronic device comprises the electronic circuit 20 having a single electrode TC wherein the fabric contact 30 made of textile material provided at the electrode TC of the electronic circuit 20, such that the electronic circuit 20 is formed a closed circuit to activate the electronic device in responsive to a physical touch by a human operator at the fabric contact 30.

Figure 11:
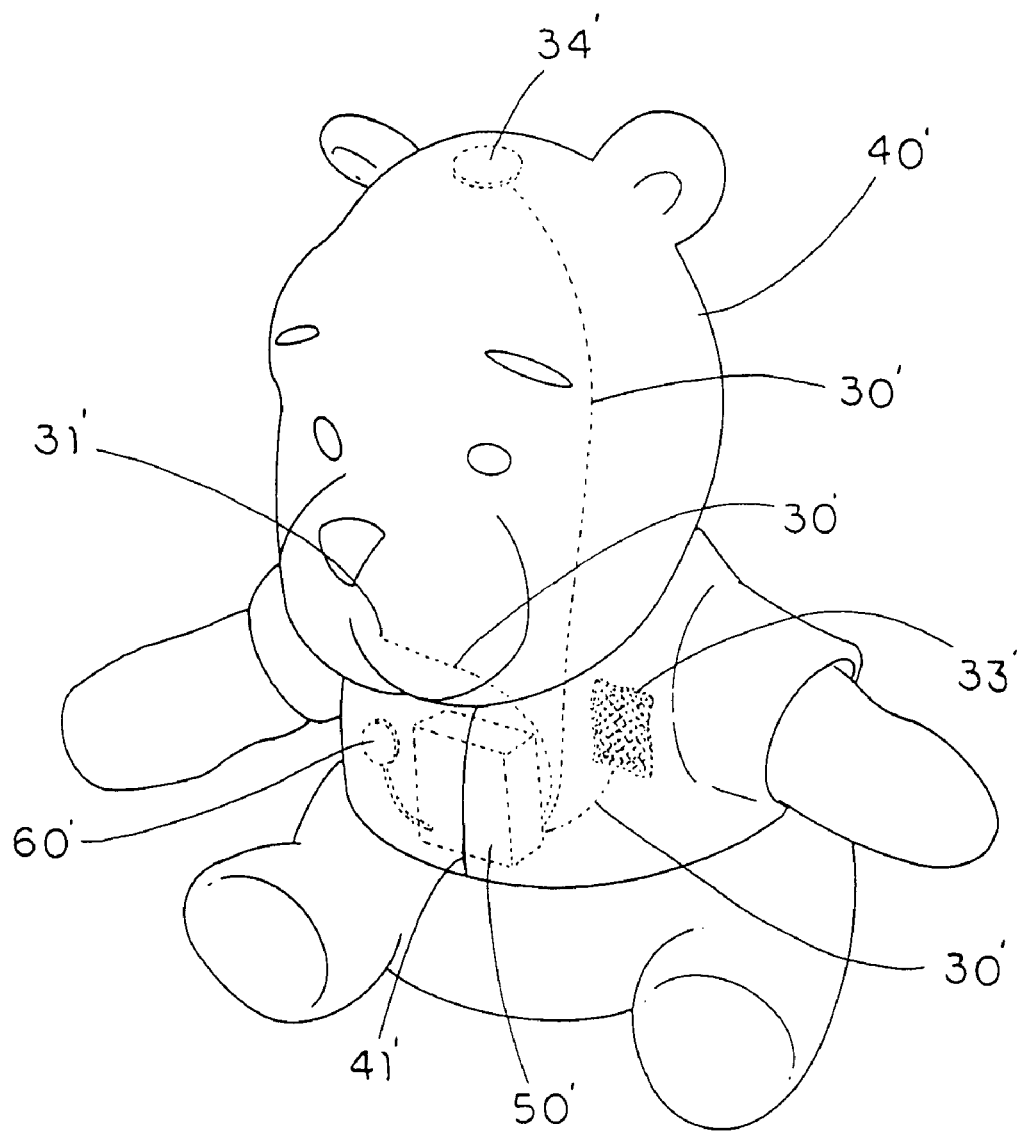
FIG. 11 illustrates an application of an activation electronic device of a children's toy according to a preferred embodiment of the present invention.
Figure 12:
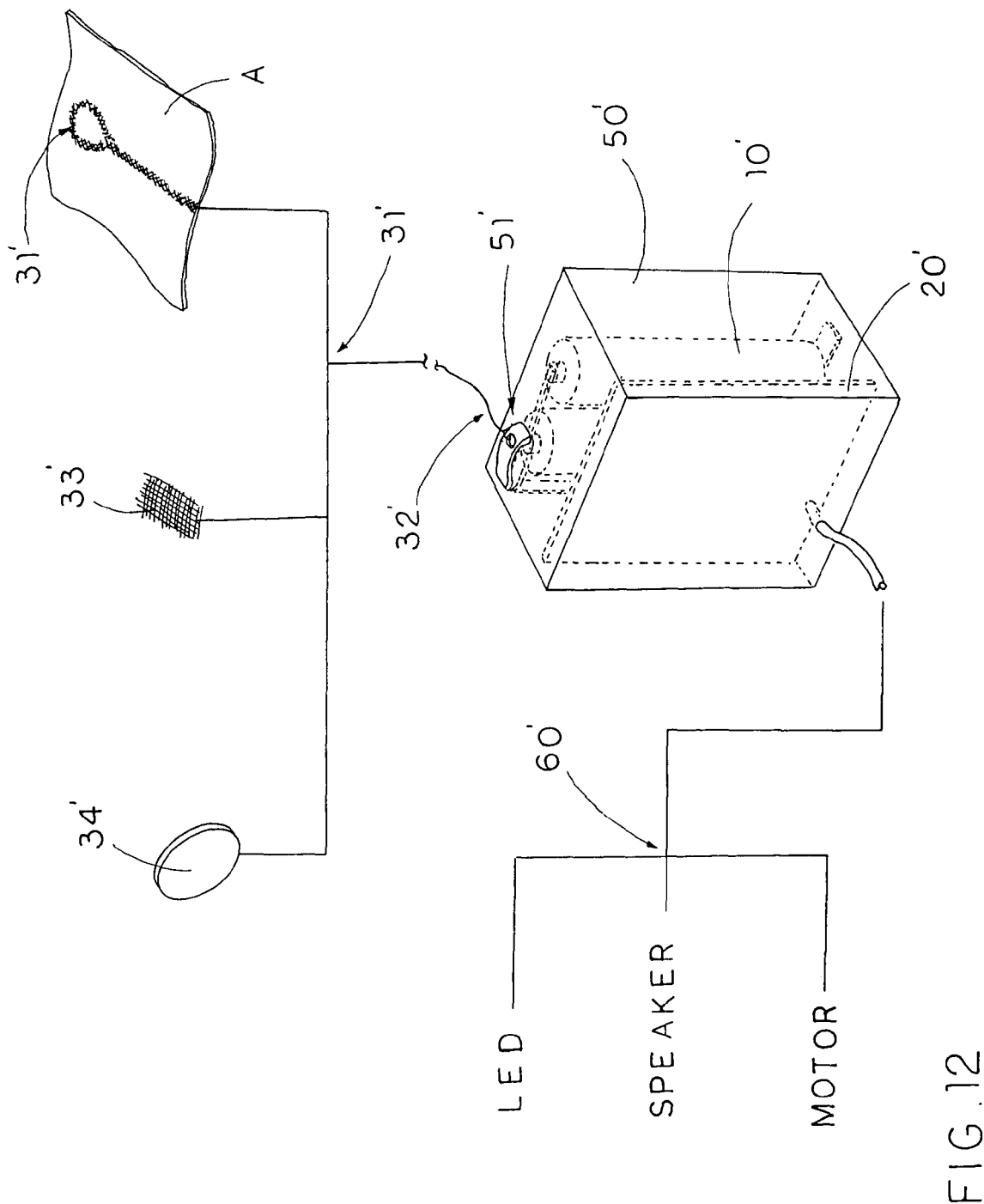
FIG. 12 illustrates an application of an activation electronic device with the conductive thread according to a preferred embodiment of the present invention.

Referring to FIGS. 11 and 12 of the drawings, an activation electronic device, especially for a low-powered activation electronic device, of an object according to a preferred embodiment of the present invention is illustrated, wherein the activation electronic device of an object comprises a power source 10', an activation circuit 20', and at least a conductive thread 30' having an electric end 32' electrically extended from the activation circuit 20' and a terminal end 31' as a terminal of the activation circuit 20', wherein the conductive thread 30' is extended within the object to activate the activation circuit 20' so as to generate an output signal. Preferably, the conductive thread 30' is a blend of stainless steel and polyester or blend of stainless steel and cotton.

According to preferred embodiment, the conductive thread 30' is made of soft washable textile material for electrical conduction. The unique properties of the conductive thread 30' make it suitable in many applications which traditional conductive materials can not replace.

Conductive thread 30' is used in traditional manner. It can be sewn as in embroidered, hand or mechanical sewn, using well known method. It serves as wiring but put in using typical sewing techniques. It can be sewn on outer layer or within the product. It can be contacted directly (surface) or indirectly (within). It is soft and flexible; it can be folded multiple times without being broken. It can be attached, sewn, or weaved onto or with other soft materials, such as textile, vinyl without introducing extra tension which gives people good contact feeling, and is safer for children. It can be used in textile made objects such as stuff toys, diaper, textile books, and so on.

The conductive thread 30' made of soft washable textile material can be washed. Doesn't like traditional conductive materials, conductive thread will not rust, it can be washed with the object it is attached, or interact with liquid such as urine and rain. Objects with conductive thread can be washed frequently.

The terminal ends 31' of the conductive thread 30' can form a point terminal, a line terminal, a layer terminal, or even a three dimensional terminal. After all, the cost of the conductive thread 30' is much less than other fabric conductive materials, it can be widely used in many fields.

As shown in FIGS. 11 and 12, the activation electronic device of the present invention is used in a stuff animal 40' according to a preferred embodiment. The power source 10' and the activation circuit 20' are adapted for being disposed in a housing 50', wherein the housing 50', which is detachably disposed in the stuff animal 40', has an electric conductor 51' electrically coupling with the activation circuit 20' to detachably contact with the electric end of the conductive thread 30'. An opening 51' of the housing 50' can be opened and closed for dispose the power source 10' and the activation circuit 20'.

The conductive thread 30' is made of soft washable textile material. One terminal end is a point terminal 31' of the conductive thread is extended to the mouth of the stuff animal 40'. It can sense conductive fluid. For example, when children feed the stuff animal 40' with water, the point terminal 31' will active the activation circuit 20'. Likewise, when two or more conductive threads 30' are extended from the activation circuit 20', a second terminal end 31' can be sewn as a textile layer terminal 33', as shown in FIGS. 11 and 12, which is underneath the outer surface of the stuff animal 40'. It activates the activation circuit when people hug or touch the stuff animal 40' over certain area of the stuff animal 40'. The third terminal end 31' is electrically coupled with a CAP sensor 34' which can detect human signals with relatively high sensitivity, and to active the activation circuit. When the activation circuit is activated, it drives the output device 60'. It is worth mentioning that the terminal end 31' of the conductive thread 30' can be sewn to form an inner lining of the stuff animal 40' to position under the outer side thereof. In addition, the conductive thread 30' can be sewn on the inner lining A of the object, such as clothing, as shown in FIG. 12.

Referring to FIG. 12, the power source 10' is a replaceable battery set. The activation circuit 20' comprises a PCB board. Both the power source 10' and the activation circuit 20' are contained in a housing 50'. The housing 50', which is detachably disposed in the stuff animal 40', has plurality of electric conductors 51' electrically coupling with the activation circuit 20' to detachably contact with the electric ends of the conductive thread 30'.

The conductive thread 30' extends and forms the terminal ends. The terminal end 31' is a point terminal, or sewn on other soft layers. The terminal end 32' is a textile layer. The terminal end 31' electrically couple with a CAP sensor 34'. Other conductive wire or the mentioned conductive thread 30' can be used for electrically coupling with the output device 60'. In an alternative embodiment, the output device 60' can be LED, speaker, motor, or like.

In an alternative embodiment, this activation electronic device can be used in a car seat with sensor, so car seat can play music or sounds when body in the car seat.

In an alternative embodiment, this activation electronic device can be used in a diaper which can detect the urine as the conductive fluid and send warning signals.

In an alternative embodiment, this activation electronic device can be used in a textile book. The power source and the circuit board can be removed from the housing and the textile book can be washed.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An activation electronic device of an object, comprising:
a power source disposed in said object;
an activation circuit disposed in said object and electrically connected with said power source for generating an output signal;
at least a conductive thread which is extended within said object, having an electric end electrically extended from said activation circuit and a terminal end as a terminal of said activation circuit;
an output device electrically coupled with said activation circuit; and
a sensor provide at said terminal end for detecting a predetermined condition and activating said activation circuit so as to generate said output signal to drives said output device.

2. The activation electronic device, as recited in claim 1, wherein said sensor is a point terminal of said activation circuit formed at said terminal end of said conductive thread is extended underneath an outer surface of said object.

3. The activated electronic device, as recited in claim 2, wherein said conductive thread is sewn on an inner lining of said object underneath said outer surface thereof.

4. The activation electronic device, as recited in claim 3, wherein said conductive thread is made of soft washable textile material for electrical conduction.

5. The activation electronic device, as recited in claim 2, wherein said activation circuit is activated via said terminal end of said conductive thread when said terminal end of said conductive thread contacts with a conductive fluid.

6. The activation electronic device, as recited in claim 2, further comprising a housing receiving said power source and said activation circuit, wherein said housing, which is detachably disposed in said object, has an electric conductor electrically coupling with said activation circuit to detachably contact with said electric end of said conductive thread.

7. The activation electronic device, as recited in claim 2, wherein said output device comprising an output element selected from a group consisting of one or more LED lighting, speaker and motor.

8. The activation electronic device, as recited in claim 1, wherein said sensor is a CAP sensor electrically coupling with said terminal end of said conductive thread, wherein said CAP sensor has a relatively high sensitivity for detecting a human signal to activate said activation circuit to drives said output device.

9. The activation electronic device, as recited in claim 8, wherein said activation circuit is activated via said terminal end of said conductive thread with respect to a human contact.

10. The activation electronic device, as recited in claim 9, wherein said conductive thread is made of soft washable textile material for electrical conduction.

11. The activation electronic device, as recited in claim 8, further comprising a housing receiving said power source and said activation circuit, wherein said housing, which is detachably disposed in said object, has an electric conductor electrically coupling with said activation circuit to detachably contact with said electric end of said conductive thread.

12. The activation electronic device, as recited in claim 8, wherein said output device comprising an output element selected from a group consisting of one or more LED lighting, speaker and motor.

13. The activation electronic device, as recited in claim 1, wherein said terminal end of said conductive thread being sewn to form a textile layer positioned underneath an outer surface of said object to form a surface terminal as said sensor of said activation circuit.

14. The activation electronic device, as recited in claim 13, further comprising a housing receiving said power source and said activation circuit, wherein said housing, which is detachably disposed in said object, has an electric conductor electrically coupling with said activation circuit to detachably contact with said electric end of said conductive thread.

15. The activation electronic device, as recited in claim 13, wherein said output device comprising an output element selected from a group consisting of one or more LED lighting, speaker and motor.

16. The activated electronic device, as recited in claim 1, wherein said conductive thread is sewn on an inner lining of said object underneath an outer surface thereof.

17. The activation electronic device, as recited in claim 1, wherein said conductive thread is made of soft washable textile material for electrical conduction.

18. The activation electronic device, as recited in claim 17, wherein said output device comprising an output element selected from a group consisting of one or more LED lighting, speaker and motor.

19. The activation electronic device, as recited in claim 1, further comprising a housing receiving said power source and said activation circuit, wherein said housing, which is detachably disposed in said object, has an electric conductor electrically coupling with said activation circuit to detachably contact with said electric end of said conductive thread.

20. The activation electronic device, as recited in claim 1, wherein said output device comprising an output element selected from a group consisting of one or more LED lighting, speaker and motor.

* * * * *